United States Patent [19]

Csizer et al.

[11] Patent Number: 4,578,270

[45] Date of Patent: Mar. 25, 1986

[54] PROCESS FOR THE PREPARATION OF LYOPHILIZED, ADSORBED POLYVALENT VACCINES

[75] Inventors: Zoltan Csizer; Karoly Sikos; Laszlo Bacskai; Istvan Joo; Eleonora Niedermayer; Lajos Rethy; Jozsef Zsidai, all of Budapest, Hungary

[73] Assignee: Human Oltoanyagtermelo Es Kutato Intezet, Budapest, Hungary

[21] Appl. No.: 582,432

[22] Filed: Feb. 22, 1984

[30] Foreign Application Priority Data

Feb. 22, 1983 [HU] Hungary .................. 609/83

[51] Int. Cl.$^4$ ............................................. A61K 39/02
[52] U.S. Cl. ...................................... 424/92; 424/101
[58] Field of Search ....................... 424/89, 92, 101

[56] References Cited

U.S. PATENT DOCUMENTS

| | | | |
|---|---|---|---|
| 2,085,391 | 6/1937 | Reichel | 424/101 X |
| 3,595,753 | 7/1971 | Stejskal et al. | 424/92 X |
| 3,599,150 | 8/1971 | Feinberg et al. | 424/92 X |
| 3,743,720 | 7/1973 | Fosker et al. | 424/92 X |
| 3,983,229 | 9/1976 | Relyveld | 424/92 |
| 4,007,265 | 2/1977 | Helting | 424/92 |
| 4,157,389 | 6/1979 | Homma et al. | 424/92 |
| 4,273,762 | 6/1981 | McAleer et al. | 424/89 |

FOREIGN PATENT DOCUMENTS

| | | | |
|---|---|---|---|
| 928807 | 6/1963 | United Kingdom | 424/92 |
| 1152607 | 5/1969 | United Kingdom | 424/92 |
| 2135190 | 8/1984 | United Kingdom | 424/92 |

Primary Examiner—Howard E. Schain
Attorney, Agent, or Firm—Karl F. Ross; Herbert Dubno

[57] ABSTRACT

The invention relates to the preparation of lyophilized, absorbed polyvalent vaccines. According to the invention tetanus, diphtheria, pertussis and optionally typhus antigens concentrated to 5 to 15 doses/3 ml are adsorbed at a pH value of 3 to 6 to an insoluble carrier concentrated in the same way as the antigens, then the pH of the mixture is adjusted to a value of 5 to 6 and lyophilized together with a protective material commonly used in lyophilizing processes. Before administration the lyophilized vaccine is diluted to the concentration required by a physiological saline buffered to a pH value of 6.8 to 7 by a phosphate solution.

10 Claims, No Drawings

PROCESS FOR THE PREPARATION OF LYOPHILIZED, ADSORBED POLYVALENT VACCINES

FIELD OF THE INVENTION

This invention relates to the preparation lyophilized, adsorbed polyvalent vaccines.

BACKGROUND OF THE INVENTION

The polvalent vaccines, e.g. the diphtheria-tetanus-pertussis (in the following: Di-Te-Pe) vaccine, play an important role in the extended vaccination program of the World Health Organization (WHO). The aim of this program is to prevent the most dangerous infectious diseases of childhood by vaccination. However, the effectivity of the vaccines commercially available at present is diminished during storage. Particularly under tropic conditions, these Di-Te-Pe vaccines can only be stored for a very short time period; as a consequence of the heat sensitivity of the pertussis component these are only stable for about 1 to 2 weeks.

During the past years, the inventors have studied the stability of the pertussis and Di-Te-Pe vaccines in detail [Csizér Z., Joó I., Zsidai J., Hegedüs L.: J. Biol. Standard 1, 347 (1973); Csizér Z., Zsidai J., Joó I.: Atca Microbiol. Acad. Sci. Hung. 22, 83 (1975); Csizér Z., Zsidai J., Joó I.: Acta Microbiol. Acad. Sci. Hung. 25, 1 (1978)] and carried out 400 active immunization experiments on mice by using 53 pertussis strain suspension mixtures within the period from 1960 to 1973. It was determined by the statistical analysis of these investigations that, when stored at 5° to 10° C., the activity of the suspensions decreased after 8 years below the value of 4 international units (IU) which is a single human dose for immunization. From 1968 to 1974, 207 active immunization experiments were carried out by using 21 Di-Te-Pe vaccines on mice. It could be stated from the statistical analysis of the results that, when stored at 5° to 10° C., the activity after 6 years of the pertussis component meets the international and domestic requirements [WHO Techn. Rep. Ser. 638, 37 (1979); Hungarian Pharmacopoeia VI. (1967)]. The mean decrease per one year in the activity of the pertussis strain suspension mixtures is 1.01 IU, while that of the pertussis component of the Di-Te-Pe vaccines is 0.35 IU. Thus, a storage at 5° to 10° C. is suitable to maintain the activity. When stored at 37° C., the activity of the vaccines significantly diminishes within 2 weeks, and even this storage temperature is also difficult to assure under tropical conditions.

OBJECT OF THE INVENTION

The scope of the invention is to provide a process for the preparation of polyvalent vaccines that can be stored under various climatic conditions for an appropriately long period.

DESCRIPTION OF THE INVENTION

The invention is based on the discovery that polyvalent vaccines of good quality, meeting the above requirements can be obtained by adsorbing the properly concentrated antigens to a carrier concentrated in the same way as the antigens, in a solution at a pH value approximating that of the isoelectric point of the antigens and by lyophilizing the obtained vaccine at a pH value causing no significant desorption. On application, the lyophilized vaccine is reconstituted by a buffer providing the adjustment to a neutral pH of the vaccine.

Accordingly, this invention relates to the preparation of lyophilized, adsorbed polyvalent vaccines.

According to our invention the tetanus, diphtheria, pertussis, and optionally typhus antigens are concentrated, adsorbed to a carrier concentrated in the same way as the antigens at a pH of 3 to 6, the pH of the combined solutions is adjusted to a value of 5 to 6 and the mixture is lyophilized.

It is well-known that the optimum adsorption of the antigens proceeds at a pH value approximating their isoelectric point, while the antigens are eluated at a pH value which is much higher than their isoelectric point. The adsorption conditions of the tetanus toxoid as a function of the pH value are shown in the following table.

TABLE 1

| pH | Aluminum phosphate HOLT* | Aluminum phosphate ERICKSON* | Aluminum hydroxide |
|---|---|---|---|
| 3.0 | 100 | 100 | not measurable |
| 3.5 | 100 | 95 | not measurable |
| 4.0 | 90 to 100 | 80 to 85 | not measurable |
| 4.5 | 85 to 90 | 60 to 70 | not measurable |
| 5.0 | 80 to 85 | 60 to 70 | 100 |
| 5.5 | 80 to 85 | 60 to 70 | 100 |
| 6.0 | 80 to 85 | 50 to 60 | 100 |
| 7.0 | 20 | 10 | 100 |
| 7.5 | no adsorption | | 85 |
| 8.0 | no adsorption | | 70 |
| 8.5 | no adsorption | | 70 |

*Note:
Methods for the preparation of aluminum phosphate.

In the course of our experiments, the carrier was used in an amount equal to 1 mg of $Al^{3+}$ ions per 1 ml, while 10 BU (binding unit) of tetanus toxoid were employed. The data of the table express the percentage of the adsorption as related to the tetanus toxoid employed.

It is also known that the common pH value of a polyvalent antigen solution should not be lower on adsorption than is the isoelectric value characteristic of the individual antigens. Simultaneously, the common pH value should not exceed a pH value at which more than 15 percent of the antigens, adsorbed at the pH value of the isoelectric point, are eluated.

The pH value is suitably adjusted by using sodium hydroxide or hydrochloric acid solution, respectively.

Preferably, aluminum phosphate or aluminum hydroxide gel can be applied as insoluble carrier, in an amount determined in preliminary experiments. In the course of these investigations, various amounts of the carriers are added to solutions containing the antigen in various concentrations and the immunizing capability of the model vaccines obtained is measured. On investigation e.g. of the immunizing power of the tetanus toxoid in guinea pigs by using an aluminum hydroxide carrier, the results shown in Table 2 were obtained.

TABLE 2

| Aluminum hydroxide mg/dose | Average of the titer of the tetanus antitoxin after a single immunization | | |
|---|---|---|---|
| | 14th day | 28th day | 42nd day |
| 0.625 | 0.4 | 0.8 | 1.2 |
| 1.25 | 0.8 | 1.9 | 2.6 |
| 2.5 | 0.8 | 5.0 | 6.0 |
| 5.0 | 1.5 | 8.0 | 8.0 |
| 10.0 | 0.5 | 4.0 | 3.0 |
| 20.0 | 0.2 | 0.5 | 1.0 |

On the basis of the mathematical evaluation of the results obtained, the optimum amount of aluminum hydroxide proved to be 3.1 mg, 3.06 mg and 3.44 mg, respectively.

By using a model vaccine containing 5 BU of tetanus toxoid and 5 Lf (limes flocculans) of diphtheria toxoid, the following results were obtained.

TABLE 3

| Aluminum hydroxide | Average of the titer of the diphtheria after a single immunization | | |
|---|---|---|---|
| mg/dose | 14th day | 28th day | 42nd day |
| 0.625 | 0.03 | 0.3 | 0.4 |
| 1.25 | 0.12 | 0.8 | 0.8 |
| 2.5 | 0.2 | 1.6 | 1.6 |
| 5.0 | 0.2 | 1.8 | 2.0 |
| 10.0 | 0.04 | 0.3 | 0.6 |

On the basis of mathematical evaluation of the results, the optimum amount of aluminum hydroxide proved to be 2.72 mg, 2.78 mg and 3.0 mg, respectively.

Similar experiments were carried out with aluminum phosphate as a carrier, too. As a result of summarizing our experimental results it can be stated that the preferable amount of both carriers is between 1.75 and 3.5 mg per dose.

According to the invention the concentrated individual antigens are adsorbed from separate solutions to the carrier concentrated in the same way as the antigens, at the optimum pH value characteristic of the individual antigens. Thus, the tetanus toxoid is adsorbed at about pH 3, diphtheria toxoid at about pH 4 and pertussis and typhus antigens at about pH 5.8 to 6. Alternatively, the adsorption can also be accomplished in the combined solution of the antigens.

It is known that the physical and chemical properties of aluminum phosphate and aluminum hydroxide gels are altered during the lyophilization. The particle size significantly increases, while the adsorption capacity is diminished. However, the physico-chemical characteristics of the gels can be kept by using an appropriate protective material.

Suitable protective materials are e.g. proteins, polypeptides, polysaccharides and other synthetic protective colloids. The most important requirements against the used protective materials are the inertness from chemical, immunological and pharmacological points of view and on the other hand the absence of toxicity.

The appropriately concentrated and adsorbed antigen also exerts an important protective effect as a consequence of its proteinous nature. It was observed in the course of our experiments that the antigen concentration is suitable when 10 doses of the vaccine are dissolved in a total volume of 3 ml; however, an other protective material is also required. These two effects together provide a satisfying protection during lyophilization. According to our experiments, dextran with a molecular weight of 40,000 or the combination of dextran with polysaccharides, respectively proved to be most convenient for this purpose.

The physico-chemical properties of the carrier can well be characterized by the sedimentation rate after reconstitution following the lyophilization. The results of our experiments relating to the combined effect exerted by the antigen protein and dextran on the physicochemical properties of the aluminium phosphate carrier during lyophilization are summarized in Table 4.

TABLE 4

| Protein amount mg/ml | Dextran % | Sedimentation (mm) | | | |
|---|---|---|---|---|---|
| | | 15 min | 30 min | 5 min | 30 min |
| | | before lyophilization | | after lyophilization | |
| 0 | 0 | 3 | 14 | sand-like | |
| 0.2 | 0 | 3 | 14 | sand-like | |
| 0.8 | 0 | 3 | 15 | sand-like | |
| 3.2 | 0 | 4 | 13 | sand-like | |
| 13.0 | 0 | 4 | 10 | several phases | |
| 50.0 | 0 | 1 | 8 | 50 | 100 |
| 0 | 1 | 4 | 15 | sand-like | |
| 0.2 | 1 | 3 | 14 | sedimentation in several | |
| 0.4 | 1 | 3 | 15 | phases with a sand-like | |
| 0.8 | 1 | 3 | 14 | aggregation | |
| 1.6 | 1 | 3 | 15 | 100 | homogeneous |
| 3.2 | 1 | 3 | 14 | 100 | homogeneous |
| 6.4 | 1 | 3 | 14 | 100 | homogeneous |
| 13.0 | 1 | 2 | 5 | 45 | 100 |
| 26.0 | 1 | 2 | 6 | 25 | 45 |
| 50.0 | 1 | 1 | 4 | 10 | 23 |
| 0 | 2 | 4 | 14 | 28 | 72 |
| 0.2 | 2 | 3 | 14 | 30 | 65 |
| 0.4 | 2 | 3 | 14 | 30 | 66 |
| 0.8 | 2 | 3 | 13 | 20 | 60 |
| 1.6 | 2 | 3 | 14 | 20 | 55 |
| 3.2 | 2 | 3 | 15 | 20 | 40 |
| 6.4 | 2 | 4 | 16 | 10 | 20 |
| 0 | 4 | 3 | 14 | 15 | 50 |
| 0.2 | 4 | 3 | 15 | 15 | 45 |
| 0.4 | 4 | 3 | 14 | 10 | 45 |
| 0.8 | 4 | 3 | 14 | 10 | 40 |
| 1.6 | 4 | 3 | 14 | 8 | 30 |
| 3.2 | 4 | 3 | 14 | 6 | 16 |
| 6.4 | 4 | 3 | 13 | 6 | 14 |

Accordingly, 0.5 to 10 percent by weight of protective material and 0.01 percent by weight of thiomersal as preservative are added to the solution of the antigens. The mixture obtained is portioned in ampules and lyophilized in such a way that the temperature of the material does not exceed $-30°$ C., preferably $-35°$ C. at the beginning. In the second stage of the lyophilization, the temperature of the material is maintained at 30° to 35° C. in order to provide the required moisture content below 3 percent.

The lyophilized vaccine can be administered after dilution to the concentration required by a physiological saline buffered to a pH value of 6,8 to 7 by a phosphate solution.

The advantage of the process of the invention consists in that the adsorbed and lyophilized polyvalent vaccines prepared according to the invention are capable of keeping their activity for a substantially longer period than the commercially available vaccines do. The Di-Te-Pe vaccine prepared by the process of our invention can be stored on the basis of our experiments for at least 4 weeks at 56° C. and for at least one year at 37° C. without any decrease in their activity.

SPECIFIC EXAMPLES

The following examples will further illustrate the invention without however limiting it there to.

EXAMPLE 1

*Bordatella pertussis* suspensions grown in a fermentor are concentrated by acidic precipitation by using 1N hydrochloric acid at a pH value of about 4, then the suspensions are settled at 4° C. for 48 hours. After decanting the supernatant, the sediment is resuspended in an isotonic saline solution buffered to pH 7.2 in such a way that the capacity of the suspension is adjusted to 300 IOU/ml (international opacity unit). The suspensions are inactivated by 0.02 percent by weight of thiomersal and by a heat treatment at 56° C. for 30 minutes and then stored at 4° C.

EXAMPLE 2

Vaccines are prepared with the following ingredients (the amounts relate to 10 doses in a total volume of 3 ml).

|  | 1 | 2 | 3 | 4 | 5 | 6 | 7 |
|---|---|---|---|---|---|---|---|
| Diphtheria toxoid (Lf)* | 250 | 250 | 250 | 250 | 300 | 300 | 300 |
| Pertussis cell suspension (IOU)* | 150 | 150 | 150 | 150 | 150 | 150 | 150 |
| Tetanus toxoid (BU)* | 50 | 50 | 100 | 100 | 100 | 100 | 100 |
| *Salmonella typhi* (cells) | — | $5 \times 10^9$ | — | — | — | — | — |
| Aluminum phosphate gel (mg) | 30 | 30 | 30 | 30 | 30 | 30 | 30 |
| Thiomersal (% by weight) | 0.01 | 0.01 | 0.01 | 0.01 | 0.01 | 0.01 | 0.01 |
| Saccharose (% by weight) | 9 | 9 | 9 | — | 9 | — | 4.5 |
| Lactose (% by weight) | — | — | — | 9 | — | — | — |
| Dextran (% by weight) | — | — | — | — | — | 5 | 2.5 |

Note:
Lf: *Limes flocculans*
IOU: International opacity unit
BU: Binding unit

The individual antigens are separated adsorbed in aluminum phosphate, the protective material and thiomersal are added to the combined solution, the pH value of the solution is adjusted to 5 to 5.8 then each 3 ml of the solution are filled into ampoules and lyophilized. The temperature of the material is kept below −35° C. within the first 10 hours of the lyophilization, at −35° to +20° C. during the following 8 hours and at +20° to +35° C. during the last 10 hours.

EXAMPLE 3

Study of the heat tolerability of the vaccines

| Vaccine | Protective material | Activity of the pertussis component after storage (weeks) at 56° C. | at 37° C. |
|---|---|---|---|
| 5 | 9% of saccharose | 1 | 26 |
| 6 | 5% of dextran | 4 | 53 |
| 7 | 4.5% of saccharose + 2.5% of dextran | 1 | 26 |

By contrast, the activity of the pertussis component of the usually adsorbed Di-Te-Pe vaccine significantly decreases during a storage of 2 weeks at 37° C.

What we claim is:

1. A process for the preparation of lyophilized, adsorbed, polyvalent vaccine against tetanus, diphtheria and pertussis, which comprises the steps of:
    (a) concentrating tetanus, diphtheria, and pertussis antigens to a value of 5 to 15 doses of vaccine per 3 ml;
    (b) concentrating an insoluble adsorbent carrier selected from the group consisting of aluminum hydroxide gel and aluminum phosphate so that 1.75 to 3.5 mg of adsorbent carrier are employed per dose of vaccine;
    (c) adsorbing the tetanus, diphtheria, and pertussis antigens concentrated in step (a), separately or together, on the insoluble adsorbent carrier concentrated in step (b), at a pH of 3 to 6, which is not lower than the value of the isoelectric point of any of the antigens and which does not exceed a pH value at which more than 15% of the antigens adsorbed at the pH value of the isoelectric point are eluated;
    (d) adjusting the pH value to 5 to 6: and
    (e) lyophilizing the mixture in the presence of a protective material selected from the group consisting of proteins, polypeptides and polysaccharides.

2. The process defined in claim 1 wherein in step (c) separate solutions of the tetanus, diphtheria, and pertussis antigens are adsorbed on the adsorbent carrier.

3. The process defined in claim 2 wherein the tetanus antigen is adsorbed at a pH of about 3.

4. The process defined in claim 2 wherein the diphtheria antigen is adsorbed at a pH of about 4.

5. The process defined in claim 2 wherein the pertussis antigen is adsorbed at a pH of about 5.8 to 6.

6. The process defined in claim 1 wherein the polyvalent vaccine further comprises typhus antigens.

7. The process defined in claim 1 which comprises using 20 to 35 Lf/dose of diphtheria toxoid, 10 to 20 IOU/dose of *Bordatella pertussis* cell suspension and 5 to 15 BU/dose of tetanus toxoid.

8. The process defined in claim 6 which comprises using a *Salmonella typhi* cell suspension containing $10^8$ to $10^9$ cells/dose.

9. A long-term storage vaccine made by the process defined in claim 1.

10. A vaccination method which comprises inoculating a subject with the vaccine defined in claim 9.

* * * * *